United States Patent [19]
Duffy et al.

[11] Patent Number: 5,836,910
[45] Date of Patent: Nov. 17, 1998

[54] METHOD AND APPARATUS FOR LOGICAL ADDRESSING IN A MODULAR PATIENT CARE SYSTEM

[75] Inventors: Robert J. Duffy, Poway; Casimer Domitrz, San Diego; Edward M. Richards, Pleasanton; Lon M. Severe, San Diego; Benson C. Stone, Poway, all of Calif.

[73] Assignee: Alaris Medical Systems, Inc., San Diego, Calif.

[21] Appl. No.: 866,664

[22] Filed: Jun. 9, 1997

Related U.S. Application Data

[63] Continuation-in-part of Ser. No. 403,503, Mar. 13, 1995, Pat. No. 5,713,856.

[51] Int. Cl.$^6$ ..................................................... A61B 31/00
[52] U.S. Cl. ............................................................ 604/65
[58] Field of Search ................................. 604/30, 31, 49, 604/50, 65–67, 118, 246; 128/DIG. 12, DIG. 13

Primary Examiner—Michael Buiz
Assistant Examiner—Manuel Mendez
Attorney, Agent, or Firm—Pennie & Edmonds LLP

[57] ABSTRACT

A modular patient care system is described having unique mechanical, electrical, and logical features. An apparatus is described for allowing a modular connection arrangement wherein modules are detachably connected to each other in a convenient, flexible, interchangeable, and secure manner by providing a hinge connector pair, a specially located latch mechanism, and a guide means between any pair of modules. Additionally, an apparatus and method is described for automatic, sequential, and dynamic logical address assignment of functional units attached to the central management unit, according to their respective position in a linear array of units. Logical address assignment is designed to occur automatically upon a physical reconfiguration of the functional units, without requiring external input or a rearranged scheme for determining the relative physical positions of the functional units.

22 Claims, 13 Drawing Sheets

METHOD AND APPARATUS FOR LOGICAL ADDRESSING IN A MODULAR PATIENT CARE SYSTEM

CROSS REFERENCE TO RELATED APPLICATIONS

This application is a continuation-in-part of U.S. patent application Ser. No. 08/403,503, entitled "Modular Patient Monitoring and Infusion System," filed Mar. 13, 1995, now U.S. Pat. No. 5,713,856 and assigned to the assignee of the present invention. The subject matter of U.S. patent application Ser. No. 08/403,503 is incorporated herein by reference.

This application also contains subject matter related to copending U.S. patent application Ser. No. 08/871,307 filed Jun. 9, 1997 entitled "Method and Apparatus for Power Connection in a Modular Patient Care System," both assigned to the assignee of the present invention. The subject matter of this application is also incorporated herein by reference.

FIELD OF THE INVENTION

The present invention relates generally to modular patient care systems. More specifically, the present invention relates to modular connection arrangement wherein modules are detachably connected to each other in a convenient, flexible, interchangeable, and secure manner. Additionally, the present invention relates to a scheme for automatic, sequential, and dynamic logical address assignment of peripheral units attached to the central management unit.

BACKGROUND OF THE INVENTION

Systems containing multiple infusion pumping units, sensing units such as blood pressure monitors and pulse oximeters, and other patient-care units are known in the medical field. For example, Kerns et al (U.S. Pat. No. 4,756,706; "Kerns") discloses a centrally managed pump system in which pump and monitoring modules are selectively attached to a central management unit. The central management unit controls the internal setup and programming of the attached modules, and receives and displays information from them. Each module is capable of being detached from the central management unit except for the first module, which is permanently attached. Once attached and programmed, a module which is subsequently detached is still capable of operating independently of the management unit.

Kerns provides for each module having its own separate cable leading to the central management unit, this cable comprising Incoming Communication and Outgoing Communication connections (Kerns col. 5, lines 11–19). The cable for each unit achieves separate contact with the central management unit by means of pass-through structures built in to each module (Kerns FIG. 4f). Thus, the central management unit is automatically aware of the relative position of a given module in the stack by virtue of the physical port to which it is connected (Kerns col. 5, lines 32–36).

Kerns has several disadvantages. Because each module requires its own set of electrical paths to the central unit, the total number of modules which may be stacked is only one greater than the number of pass-through cables in each module. For example, for the pass-through structure shown in Kerns FIG. 4f, only four modules total may be accommodated by a system which uses these modules. Also, there is added weight, cost, and complexity due to the multiple cabling structure. For example, each signal of each cable must have its own contact pin in among the pins 122 of the contact structure of Kerns FIG. 3.

Rubalcaba (U.S. Pat. No. 4,898,578) also discloses a drug infusion system which includes a plurality of infusion pump modules selectively attached to a central management unit so as to provide for centralized control. In particular, the central management unit obtains infusion parameters from the user and then performs calculations with the parameters to establish the desired infusion rate. Once this rate is determined, the central management unit may control the infusion accordingly. Rubalcaba, however, provides no solution for the problems related to electrical and mechanical connectivity of units described above with respect to Kerns.

It has been found that a common communications bus scheme provides for lesser complexity of the modular patient care system. At the same time, however, in a system not having separate communications connections from the central unit to each peripheral module, a logical addressing scheme is necessary for identification of the peripheral units according to their physical location in the system. It is desirable that external user input not be required to achieve this identification and logical addressing.

Barbour et al (U.S. Pat. No. 3,949,380) discloses a peripheral device reassignment control technique, wherein a plurality of peripheral devices having physical addresses are accessed by a host processor by use of logical addresses which are utilized by the various programs in a multiprocessing environment. This disclosure, however, is simply related to the mapping of logical addresses into physical addresses to access peripheral devices. The disclosure presumes the existence of physical addresses for each of the peripheral devices, and therefor obviates the need for detecting the physical location of the peripheral devices for sequential logical address assignment.

Accordingly, it an object of the present invention to provide a modular patient care system wherein modules are detachably connected to each other in a convenient, flexible, interchangeable, and secure manner.

It is another object of the present invention to provide a scheme for sequential and dynamic logical address assignment of peripheral units attached to the central management unit in a modular patient care system having a common communications bus arrangement.

It is yet another object of the present invention to provide for automatic address assignment of peripheral units without the need for external user input or a predetermination regarding the relative physical location of the peripheral devices.

SUMMARY OF THE INVENTION

These and other objects of the present invention are provided for in a modular patient care system having an interface unit for providing a user interface to said system and at least one functional unit, the functional unit being capable of removable connection to the interface unit for providing patient therapies or monitoring the condition of the patient, the functional unit being for removable attachment to the interface unit or other functional units so as to form a linear array of units. The linear array of units forms a common communications bus for allowing high level communication between each functional unit and the interface unit according to a unique sequential logical ID assigned to each functional unit. The linear array of units comprises an originating end and a terminating end, and each unit has an originating side and a terminating side, the originating side of any unit being capable of removable connection to the terminating side of any other unit. In one embodiment, the originating end is the left end, and the terminating end is the right end of the linear array.

In accordance with the present invention, a method and apparatus is provided wherein the modular patient care system is capable of having the interface unit automatically and dynamically assign sequential logical ID's to the attached functional units according to their respective positions in the linear array of units. The assignment is automatic in that it does not require instructions by a user as to the relative positions of the units in the linear array. The interface unit and functional units are configured and dimensioned so as to be capable of performing a series of steps to automatically and dynamically assign the sequential logical ID's.

Generally, each functional unit has a unit detect bus portion for forming a unit detect bus. In particular, the unit detect bus portion forms a left unit detect bus, terminating at a left unit detect lead of the interface unit, for functional units attached to the left of the interface unit. However, the unit detect bus portion is bidirectional in that when the functional unit is attached to the right of the interface unit, a right unit detect bus is formed, terminating at a right unit detect lead of the interface unit. Each functional unit is capable of pulling its respective unit detect bus logically low, the unit detect bus being coupled to a pullup resistor at the interface unit, the pullup resistor in turn being connected to a constant voltage source. Each functional unit also has an ID enable in lead at its left side and an ID enable out lead at its right side. The value of signals contained on these leads may be ENABLE or DISABLE. In one embodiment, ENABLE corresponds to a logic high value, whereas DISABLE corresponds to a logic low value. The interface unit also comprises an ID enable out lead at its right side.

A key feature of each functional module is that it is designed and configured such that the ID enable in lead takes on the value of the ID enable out lead of a left adjacent unit, unless the functional unit is at the left end of the array. If the unit is at the left end of the array, the ID enable in lead automatically takes on the value ENABLE, by means of a pullup resistor connected between the ID enable in lead and a constant voltage source at the level ENABLE.

Upon receiving a first command from the interface unit over the common communications bus, all functional units set ID enable out to DISABLE and pull their respective unit detect buses low. At this point, the leftmost unit is the only functional unit which (1) detects a value ENABLE at its ID enable in lead, and (2) has not yet been assigned a logical ID after receiving the first command. The leftmost unit sends a ready-for-ID message to the interface unit over the common communications bus. In response, the interface unit sends out a sequential logical address over the common communications bus, this address being received by the leftmost unit. After receiving the logical ID, the leftmost functional unit releases its respective unit detect bus and sets its ID enable out lead to ENABLE. At this point, the next adjacent functional unit is the only functional unit which (1) detects a value ENABLE at its ID enable in lead, and (2) has not yet been assigned a logical ID after receiving the first command. The next adjacent functional unit sends a ready-for-ID message to the interface unit over the common communications bus, the interface unit sends out a sequential logical address, and the next adjacent functional unit releases its respective unit detect bus and sets its ID enable out lead to ENABLE.

When all functional units on the left side of the interface unit have been assigned logical ID's, the interface unit is so notified by detecting the releasing of the left unit detect bus. At this point, the ID enable out lead at the right side of the interface unit is set to enable. In response, the adjacent functional unit on the right side of the interface unit, if any, sends a ready-for-ID message to the interface unit over the common communications bus. The logical ID's continue to be sequentially assigned in this manner until the rightmost unit has received its logical ID and releases the right unit detect bus. The interface unit is notified that the assignment of logical ID's is complete when the right unit detect bus is so released.

DETAILED DESCRIPTION OF THE INVENTION

Figure 1:
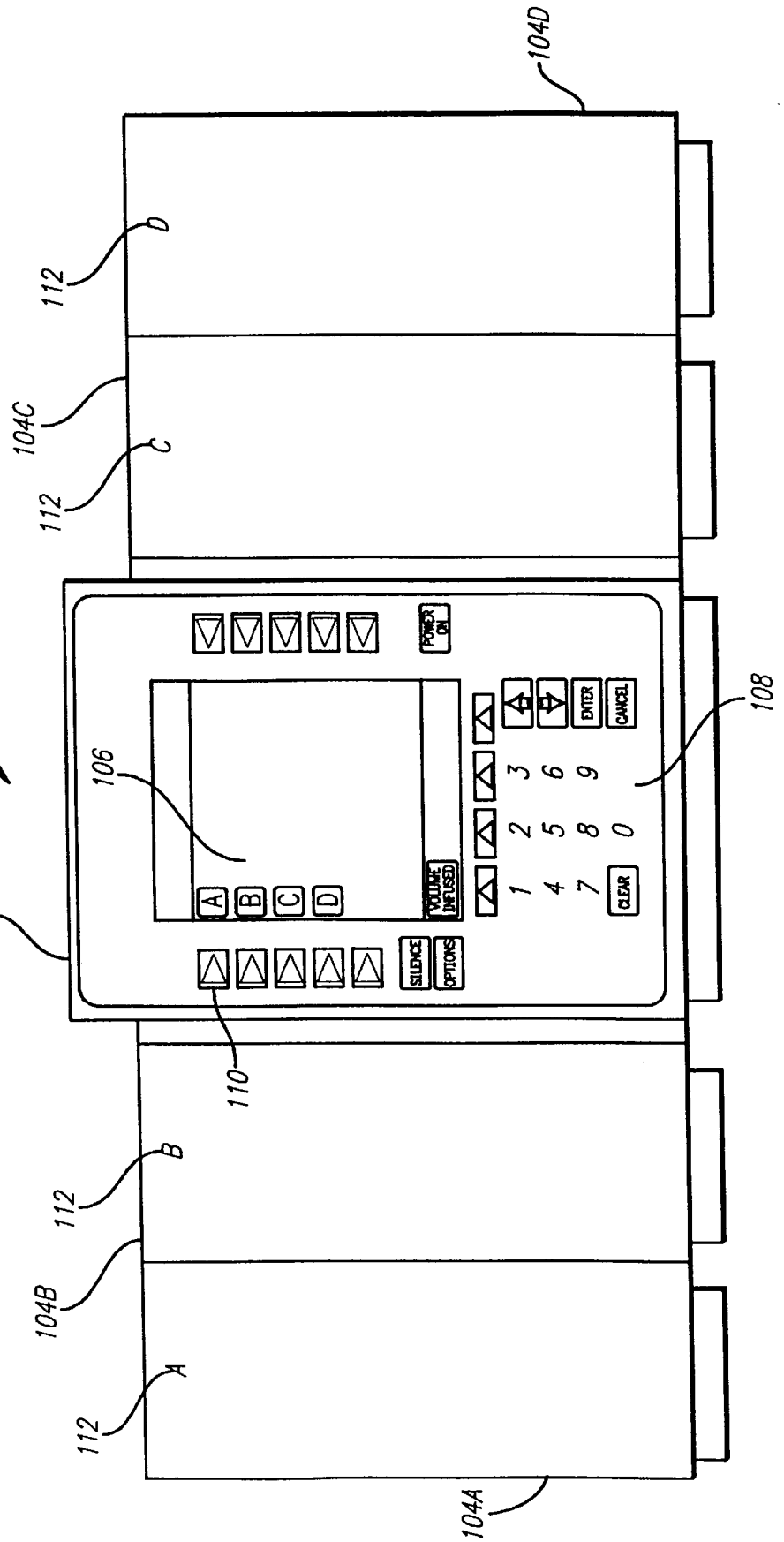
FIG. 1 is a front view of a multi-module electronic system wherein the individual modules are interconnected electrically and structurally in accordance with the present invention.

The following embodiments of the present invention will be described in the context of a modular patient care system, although those skilled in the art would recognize that the disclosed methods and structures are readily adaptable for broader application. Note that whenever the same reference numeral is repeated with respect to different figures, it refers to the corresponding structure in each figure.

FIG. 1 discloses a modular patient care system 100 in accordance with the present invention. Modular patient care system 100 comprises a plurality of modules or units, including interface unit 102 and functional units 104, detachably coupled to each other to form a linear array. Shown in FIG. 1 are exemplary functional units 104A, 104B, 104C, and 104D coupled to interface unit 102. While four functional units are shown in FIG. 1, a modular patient care system in accordance with the present invention may comprise interface unit 102 coupled to only a single functional unit 104, or may comprise interface unit 102 coupled to as many as "N" functional units 104.

Interface unit 102 generally performs the functions of (1) providing a physical attachment of the system to structures such as IV poles and bedrails, (2) providing electrical power to the system, (3) providing an interface between the system and external devices, (4) providing a user interface to the system, and (5) providing overall system control, which includes providing information to and receiving information from functional units 104. Shown in FIG. 1 are certain user interface aspects of interface unit 102, which may include an information display 106, numerical hardkeys 108, and softkeys 110.

Functional units 104 are generally for providing patient therapies or monitoring responsive to information, at least some of which may be received from interface unit 102. In many cases, functional units 104 are also for communicating information to interface unit 102. For example, functional unit 104A may be an infusion pump unit for delivering fluids to a patient responsive to certain commands received from interface unit 102, while functional unit 104B may be a blood pressure monitoring unit for providing patient blood pressure information to the interface unit 102. The scope of the invention is not so limited, however.

For the purposes of the present invention, the specific function of each individual functional unit 104 is not critical. Rather, the present invention is directed toward (1) the mechanical and electromechanical coupling of the functional units 104 to each other and to interface unit 102, and (2) the inter-unit detection and communications scheme of the modular patient care system 100. Thus, for purposes of understanding the present invention, it is important only to recognize that functional units 104 (1) require means for detachably coupling to each other and to interface unit 102, and (2) require means for communicating with interface unit 102.

In a preferred embodiment of the present invention, interface unit 102 and functional units 104 are laterally interchangeable. By laterally interchangeable, it is meant that the modules may be placed in any order in forming a linear array of modules. Thus, in FIG. 1, the modular patient care system 100 may instead have its modules ordered left-to-right in the sequence 104C, 102, 104B, 104D, 104A without affecting its functionality. In order to be laterally interchangeable, the units 102 and 104 of FIG. 1 should have substantially identical interconnection features on their respective left sides, and should have corresponding substantially identical interconnection features on their right sides. If the units were instead for coupling in a vertical linear array, which is within the scope of the present invention, the interconnection features would have substantially identical interconnection features on their respective top sides, and would have corresponding substantially identical interconnection features on their bottom sides. For clarity of explanation, however, only a left-to-right physical arrangement is described.

To achieve the lateral interchangeability described above, each of the units 102 and 104 should also have power, unit detection, and communication circuitry which is complementary. By complementary, it is meant that the units 102 and 104 generally have power, unit detection, and communications circuit contacts on a first side and on a second side, and that the first side contacts of one unit may be connected to corresponding second side contacts of any other unit, with the overall linear array of units comprising modular patient care system 100 being fully operational. In FIG. 1, for example, the first side of a unit is the left side, and the second side of a unit is the right side. Further to this example, and as further explained later, functional unit 104C must be capable of receiving electrical power from interface unit 102 to its left and transferring it to unit 104D to its right; yet, if physically interchanged with functional unit 104B, unit 104C must be capable of receiving electrical power from interface unit 102 to its right and transferring it to unit 104A to its left, and so on.

As shown in FIG. 1, each functional unit 104 may include a unit ID indicator 112 which identifies a logical address of the functional unit within the linear array. The logical address of a functional unit 104 indicates its position in the linear array relative to other functional units 104. The logical address of a functional unit 104, such as unit 104B, is used by the interface unit 102 to identify and uniquely communicate with functional unit 104B in a common communications bus environment to be described later. In a preferred embodiment of the invention, the logical address of a functional unit corresponds to its sequential position in the linear array of functional units. Thus, the system shown in FIG. 1 may illustratively contain functional units 104A–104D with logical addresses A, B, C, and D, ordered left to right. In this embodiment, the left side of the leftmost unit forms an originating end of the linear array, while the right side of the rightmost unit forms a terminating end of the linear array.

Also in a preferred embodiment of the invention, the logical address of a functional unit 104 is position-dependent, not unit-dependent. Thus, for example, in FIG. 1, if the positions of functional units 104B and 104C were physically interchanged in the linear array, the logical address of unit 104B would be changed to C, and the logical address of unit 104C would be changed to B, such that the left-to-right order of logical addresses would remain A, B, C, and D.

Figure 2:
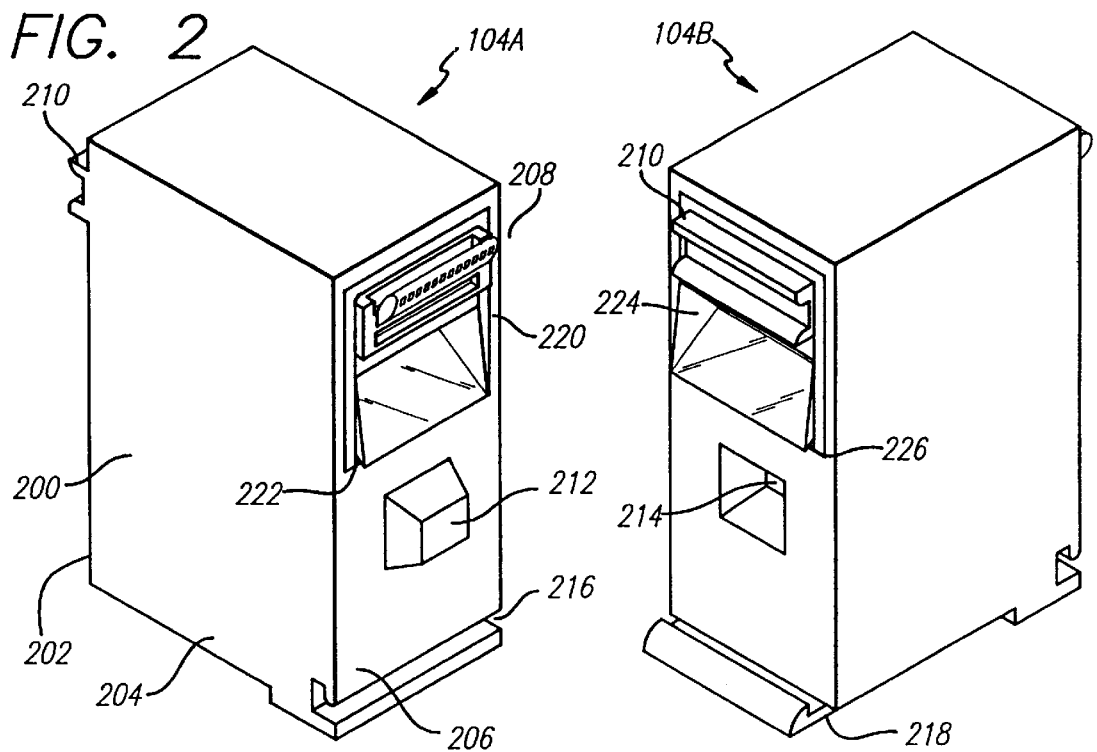
FIG. 2 shows an oblique view of two modules showing structural and electrical features for module connection in accordance with the present invention.

FIG. 2 illustrates mechanical and electromechanical aspects of interface unit 102 and functional units 104 in accordance with the present invention. For purposes of the mechanical and electromechanical aspects of the invention, interconnection features of interface unit 102 are similar to interconnection features of functional units 104 and thus only an exemplary unit 104A will be described. Also, an exemplary unit 104B, substantially identical to unit 104A and for connecting thereto, will be described when needed for clarity.

FIG. 2 shows an oblique representation of exemplary units 104A and 104B positioned before being matably connected. As shown in FIG. 2, unit 104A comprises a chassis 200 having a left side 202, a front 204, and a right side 206. It is to be appreciated that although FIG. 2 shows numbered components on units 104A and 104B according to their visibility in the oblique drawing, the units 104A and 104B contain substantially identical numbered components. Unit 104A further comprises a male connector portion 208 on right side 206, a female connector portion 210 on left side 202, a male elevation feature 212 formed on right side 206, a female recess feature 214 formed in left side 202, a catch feature 216 formed near on right side 206, and a latch 218 near left side 202. Unit 104A further comprises cover 220 tethered to male connector portion 208 for covering the male connector portion 208 during periods of non-use, and pocket 222 formed in right side 206 near male connector portion 208 for receiving cover 220 otherwise. Unit 104A further comprises cover 224 tethered to female connector portion 210 for covering female connector portion 210 during periods of non-use, and pocket 226 formed in left side 202 near female connector portion 210 for receiving cover 220 otherwise.

Male connector portion 208 of unit 104A is positioned and formed for hingeable connection with female connector portion 210 of unit 104B for achieving mechanical and electrical coupling of units 104 and 105. In a preferred embodiment of the invention, male connector portion 208 and female connector portion 210 also form a 15-pin electrical connector pair for electrically coupling. This electrical connector pair is for electrically coupling electronic components contained in units 104A and 104B.

In accordance with the present invention, functional units 104 and interface unit 102 of FIG. 1 are provided with hardware and software components for allowing (1) automatic detection of attached functional units, (2) automatic assignment of unique logical addresses of attached functional units according to their sequential position in the linear array of units, and (3) automatic detection of detachment of functional units from the system. By automatic, it is meant that associated user input is not required.

Thus, for example, in the system 100 shown in FIG. 1 which has been designed in accordance with the present invention, system 100 is capable of automatically assigning the logical addresses of A, B, C, and D to units 104A, 104B, 104C, and 104D, respectively, at initial power-up. Further, if an additional unit 104E (not shown) is later added to the right of unit 104D in the linear array while system 100 is operating, system 100 is capable of automatically assigning the logical address of E to the added unit 104E. If the additional unit 104E were instead added to the left of unit 104A, system 100 is capable of assigning a logical address of A to the added unit 104E, and capable of reassigning units 104A through 104D with the logical addresses B, C, D, and E, respectively. Finally, if one of the operating functional units 104 of FIG. 1 is removed inappropriately, system 100 is capable of sounding an alarm or entering an alarm state. By inappropriately, it is meant that interface unit 102 has not authorized removal of the removed unit responsive to a signal from the user or responsive to some other input, algorithm, or condition.

Figure 3:
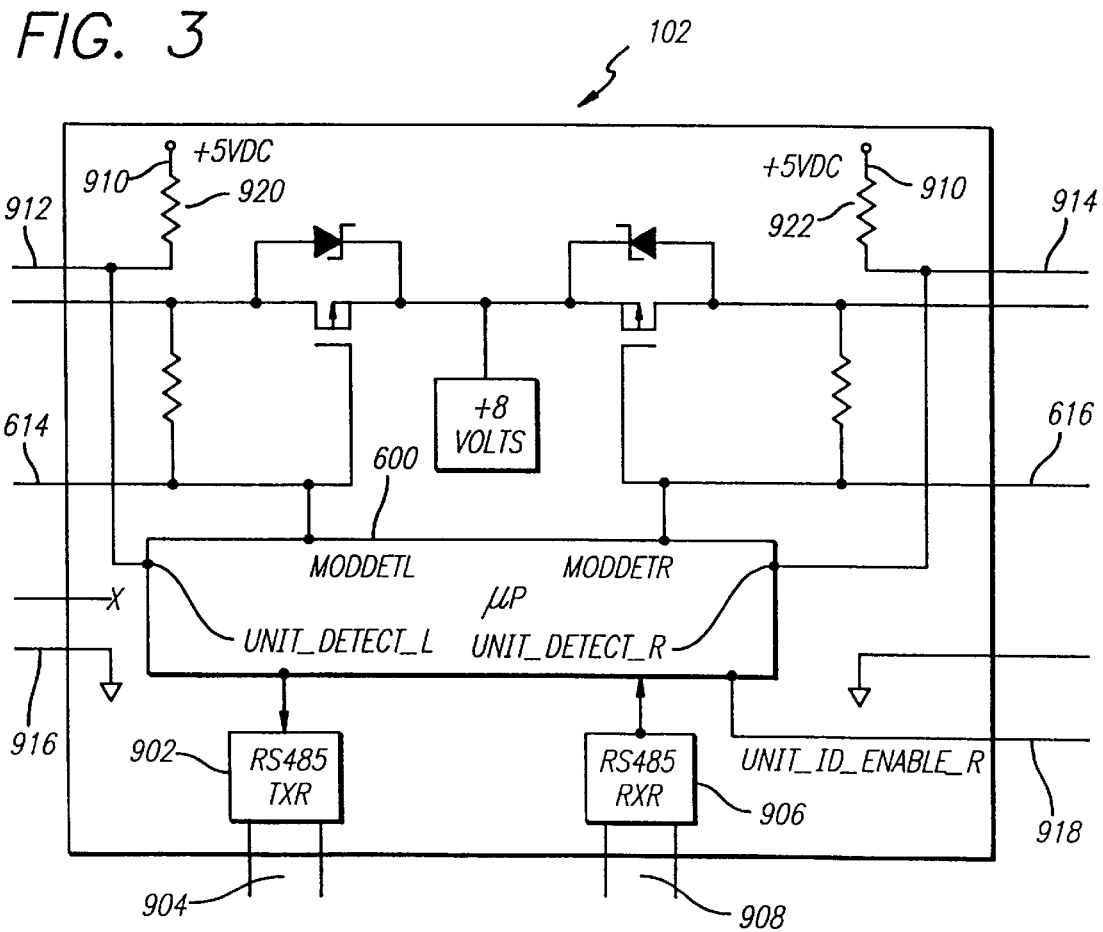
FIG. 3 shows a functional diagram of the unit identification and logical address provision features of the interface unit according to the present invention.

Referring now to FIG. 3, interface unit 102 is shown comprising a microprocessor 600, a transmitter 902, a first communications bus portion 904, a receiver 906, a second communications bus portion 908, a unit detect pullup source 910, a left unit detect lead 912, a right unit detect lead 914, an ID enable in lead 916, an ID enable out lead 918, and pullup resistors 920 and 922. These elements will be described below along with the elements of exemplary functional unit 104A as shown in FIG. 4, which comprises a microprocessor 700, a receiver 1002, a first communications bus portion 1004A, a transmitter 1006, a second communications bus portion 1008A, a unit detect bus portion 1010A, a pull-down transistor 1011, an internal pullup source 1012, and AND gate 1014, an ID enable in lead 1016, an ID enable out lead 1018, and a pullup resistor 1020.

Figure 5:
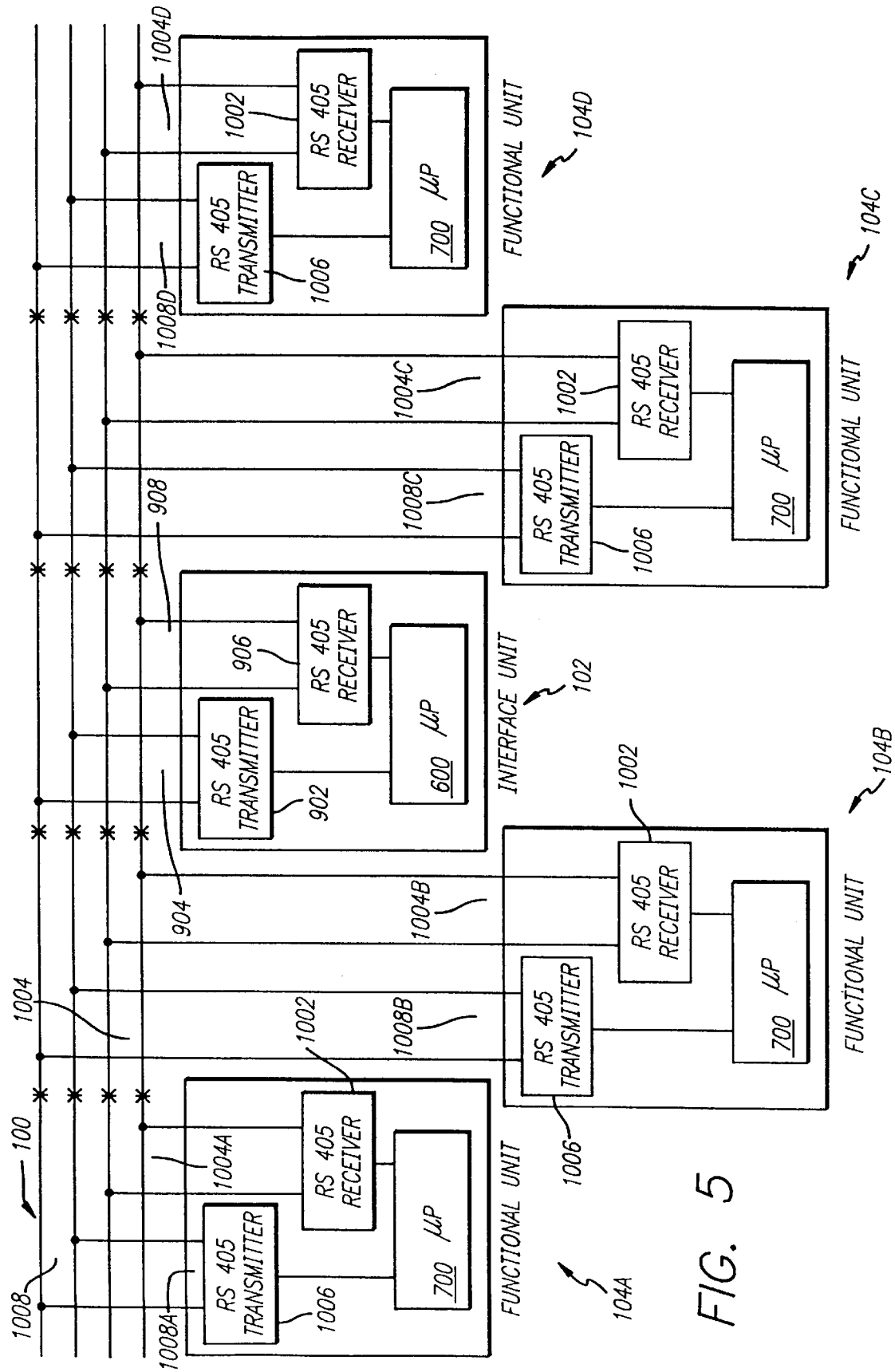
FIG. 5 shows a high-level functional block diagram of the inter-unit communications features of a modular patient care system according to the present invention.

FIG. 5 shows a symbolic diagram of the inter-unit communications scheme of system 100 in accordance with the present invention. First communications bus portions 904, 1004A, 1004B, 1004C, and 1004D of units 102 and 104 form a transmit communications bus 1004 when all units are coupled together as shown in FIG. 1. Transmit communications bus 1004 originates at transmitter 904 of interface unit 102 and couples to receivers 1002 in functional units 104, and serves as a path for information to travel from interface unit 102 to functional units 104. Second communications bus portions 908, 1008A, 1008B, 1008C, and 1008D of units 102 and 104 likewise form a receive communications bus 1008. Receive communications bus 1008 terminates at receiver 906 of unit 102 and couples to transmitters 1006 in functional units 104, and serves as a path for information to travel from each functional unit 104 to interface unit 102. The transmitters and receivers are each coupled to the microprocessor contained in their unit, as shown in FIG. 5. In general, the inter-unit communications configuration described forms a multi-drop communications connection without collision detection, as is well known in the art. In a preferred embodiment of the invention, the transmitters and receivers conform to the RS485 protocol. Also in a preferred embodiment, communications buses 1004 and 1008 are each a differential pair which allows rejection of common mode noise appearing on the signal pair. Further in a preferred embodiment of the invention, for single-fault mitigation, the transceivers and receivers on the interface unit 102 and functional units 104 are capable of switching from full-duplex operation, wherein communication on a single bus is unidirectional, to half-duplex operation, wherein communication on a single bus is bidirectional.

While the communications buses 1004 and 1008 provide the general means for high-level communications among units, further circuitry and software to provide logical address assignments to the functional units because the communications buses are incapable of detecting the relative positions of the functional units 104 and interface unit 102 in the array of units.

Figure 4:
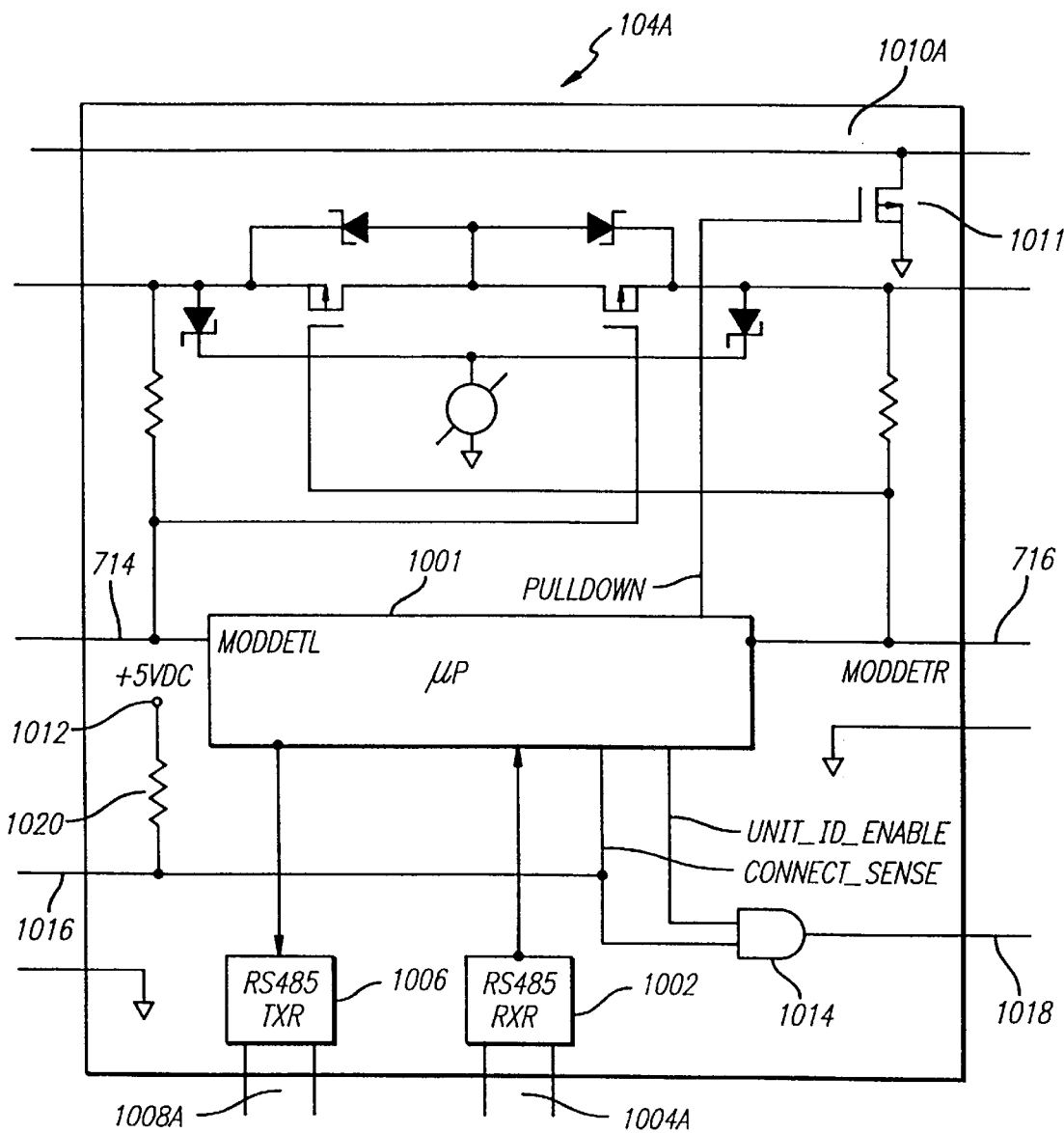
FIG. 4 discloses a functional circuit diagram of the unit identification and logical address provision features of a functional unit in accordance with the present invention.
Figure 6A:
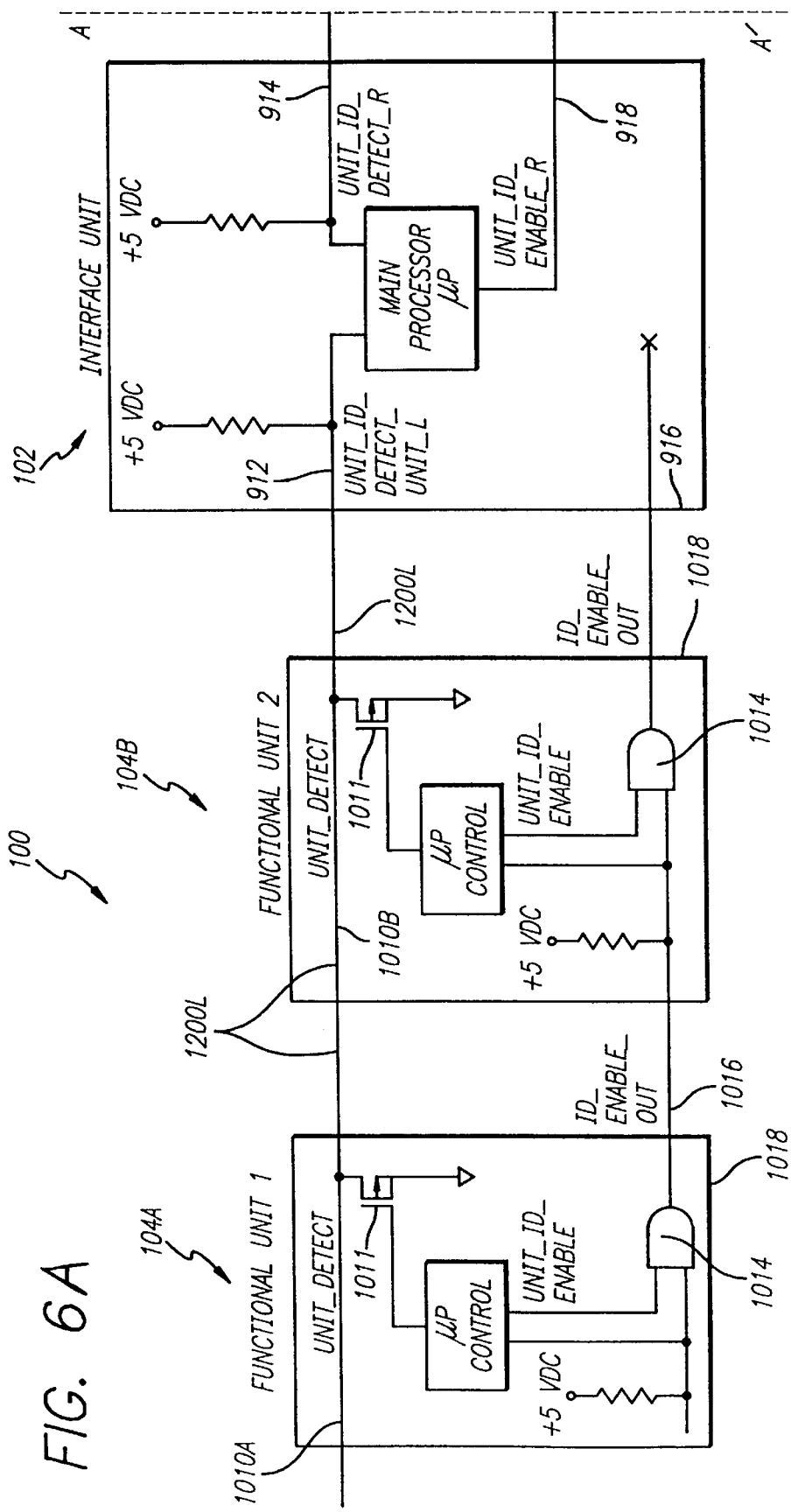
FIGS. 6A and 6B shows a functional schematic diagram of the unit detection and unit identification features of a modular patient care system in accordance with the present invention.
Figure 6B:
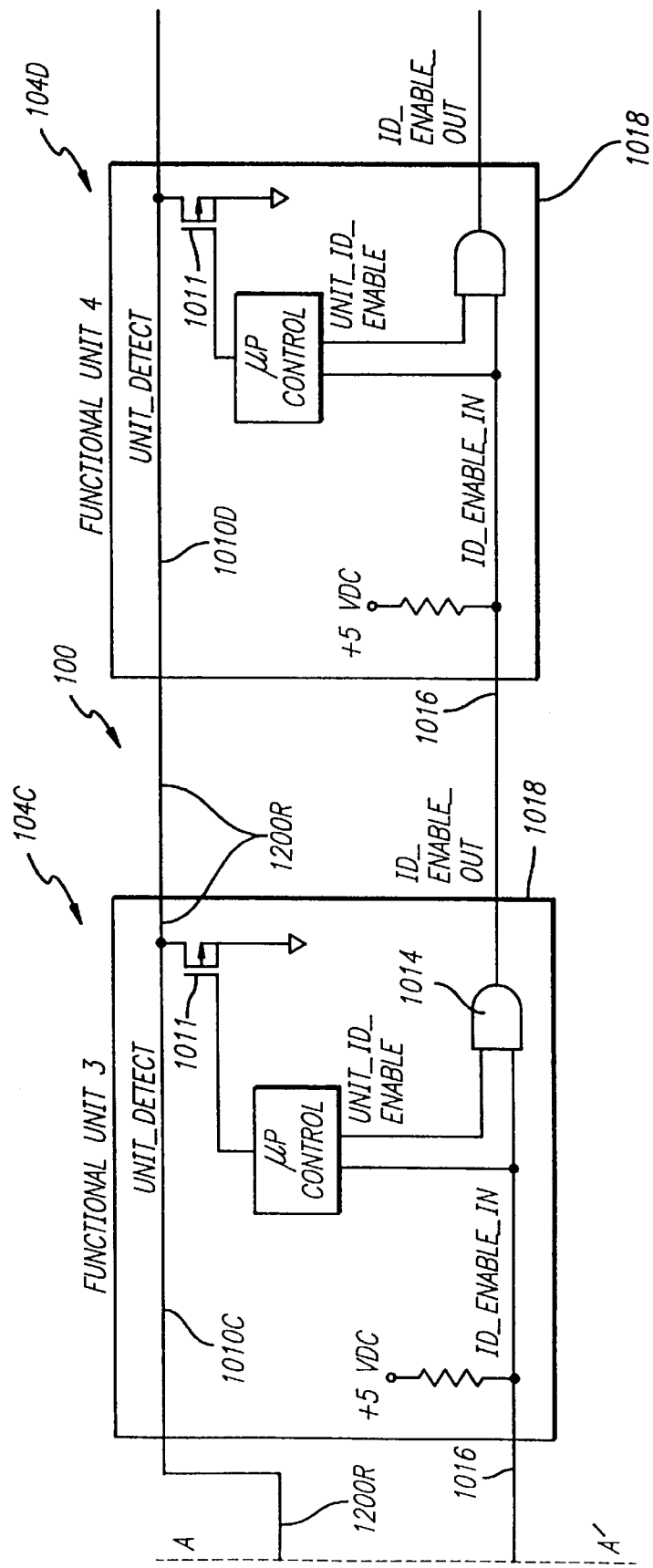

Means for achieving this result are described with reference to FIGS. 3, 4, 6A and 6B Shown in FIG. 5 is a unit detect bus portion 1010A for coupling to the unit detect bus portions of other functional units 104 and for coupling to left unit detect lead 912 or right unit detect lead 914 of interface unit 102 (FIG. 3). This coupling forms left and right unit detect buses 1200L and 1200R, as shown in FIG. 6A and 6B FIG. 3 in turn, shows unit detect pullup source 910 coupled through pullup resistors 920 and 922 to unit detect leads 912 and 914, respectively, for pulling up buses 1200L and 1200R, respectively (FIG. 6A and 6B). Finally, FIG. 4 shows pulldown transistor 1011 in exemplary functional unit 104A coupled to unit detect bus portion 1010A, and thus to unit detect bus 1200L. As shown, transistor 1011 is capable of pulling down unit detect bus 1200L or 1200R (6A and 6B), depending on which side of interface unit 102 the functional unit 104 is on, responsive to a positive signal from a PULLDOWN lead of microprocessor 700, to which it is coupled. Operationally, then, any functional unit 104 is capable of pulling down unit detect bus 1200L or 1200R responsive to software instructions executed by its microprocessor 700.

As shown in FIG. 3, interface unit comprises an ID enable in lead 916 and an ID enable out lead 918. ID enable out lead 918 is coupled to a UNIT_ID_ENABLE_R pin of a microprocessor 600 and is capable of going high or low according to instructions carried out within microprocessor 600. As shown in FIG. 4, exemplary functional unit 104A comprises ID enable in lead 1016 which is coupled to a CONNECT_SENSE pin of microprocessor 700 and to a first input of AND gate 1014. The AND gate 1014 also has a second input coupled to a UNIT_ID_ENABLE pin of microprocessor 700, which is capable of setting UNIT_ID_ENABLE high or low responsive to instructions carried out within microprocessor 700. The AND gate 1014 has an output coupled to ID enable out lead 1018, which is high only if both the ID enable in lead 1016 is high and UNIT_ID_ENABLE are high. ID enable in lead 1016 is also coupled to internal pullup source 1012 through pullup resistor 1020. A key feature of the present invention is that the resulting voltage at CONNECT_SENSE, and thus the first input of AND gate 1014, is in a high state and remains pulled up unless it is brought down by an external ground or "low" signal placed on ID enable in lead 1016.

FIGS. 6A and 6B show the interconnections of the above signals and leads of the units 104 and 102 when attached in a linear array according to the present invention. As described above, left and right unit detect buses 1200L and 1200R are formed by the respective unit detect bus portions 1010 of functional units 104 and the unit detect leads 912 and 914 of interface unit 102. Further, for any adjacent pair of units, the ID enable in lead 1016 or 916 of the unit on the right is coupled to the ID enable out lead 1018 or 918 of the unit on the left. Importantly, the ID enable in lead 1016 or 916 of the leftmost (or originating) unit is left disconnected. The ID enable out lead 1018 or 918 of the rightmost (or terminating) unit is also left disconnected.

Generally, a key to the present invention is that upon a change in configuration, a logical address is only assigned to a functional unit 104 if the microprocessor of that unit detects CONNECT_SENSE to be high. CONNECT_SENSE will only be high for (1) the leftmost unit, and (2) any unit whose ID enable in lead 1016 is not pulled down by the ID enable out lead 1018 or 916 of the unit to its left. In this way, and in a general sense, each functional unit 104 is assigned a sequential logical address by setting UNIT_ID_ENABLE to low, waiting for CONNECT_SENSE to go high, sending a ready-for-ID message to the interface unit 102 and receiving a logical address from the interface unit 102 by communicating over buses 1004 and 1008, and then setting UNIT_ID_ENABLE to high.

A description of the sequence of steps carried out by microprocessor 600 of interface unit 102 and microprocessors 700 of functional units 104 follows. It is to be recognized in the following disclosure that microprocessor 600 of interface unit 102 is capable of sending commands to microprocessors 700 of functional units 104, and receiving responses from microprocessors 700, by means of the inter-unit communications circuitry described previously. Also, it is to be recognized that microprocessor 600 of interface unit 102 is capable of sensing the following signals:

UNIT_DETECT_L corresponding to the voltage on left unit detect lead 912; UNIT_DETECT_R corresponding to the voltage on right unit detect lead 914; MODDETL corresponding to the voltage on left module detect lead 614; and MODDETR corresponding to the voltage on right unit detect lead 616. It is also to be recognized that microprocessor 600 is capable of creating a signal UNIT_ID_ENABLE_R and driving the voltage on ID enable out lead 918 according to this signal.

Further, it is to be recognized in the following disclosure that microprocessor 700 of exemplary functional module 104A is capable of receiving commands and sending responses to microprocessor 600 of interface unit 102 by means of the inter-unit communications circuitry described previously. Also, it is to be recognized that microprocessor 700 is capable of sensing: the CONNECT_SENSE signal which corresponds to the voltage at ID enable in lead 1016 and at the first input of AND gate 1014; the signal MODDETL corresponding to the voltage at left module detect lead 714; and the signal MODDETR corresponding to the voltage at right module detect lead 716. Also, it is to be recognized that microprocessor 700 is capable of the following: driving the gate of transistor 1011 to low by means of a signal PULLDOWN, therefore pulling down unit one of unit detect buses 1200L or 1200R depending on which side of interface unit 102 the functional unit 104A is positioned; and generating the second input to AND gate 104 by means of a signal UNIT_ID_ENABLE.

Figure 7:
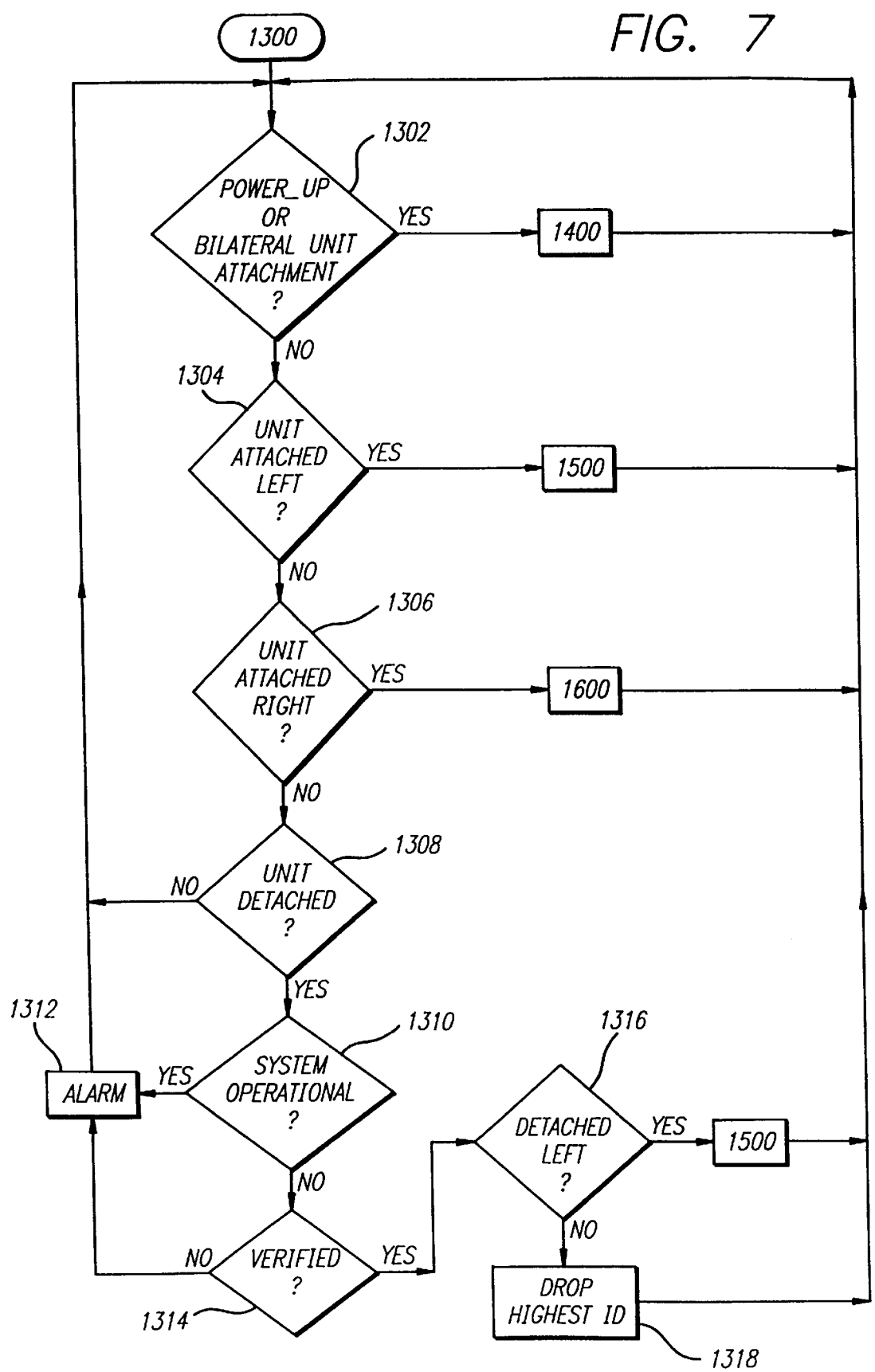
FIGS. 7, 8, 9A and 9B and 10 illustrate steps performed by the interface unit for unit identification and logical ID assignment in accordance with the present invention.
Figure 8:
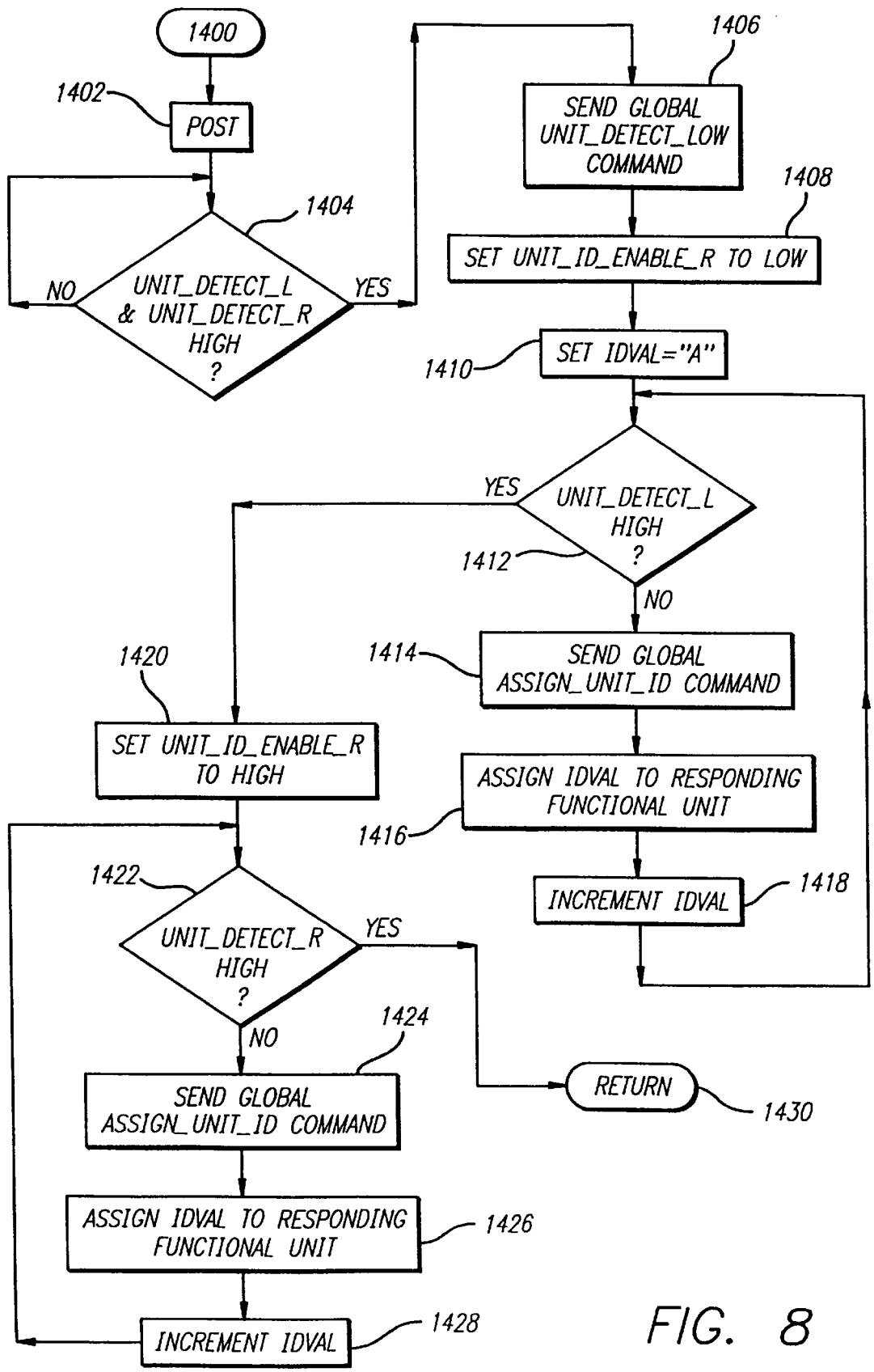

FIG. 7 illustrates steps carried out by microprocessor 600 of interface unit 102 in accordance with the present invention. Beginning at step 1300, step 1302 is first performed. Step 1302 comprises steps, beyond the scope of the present disclosure but capable of being programmed by a person of ordinary skill in the art, wherein microprocessor 600 detects if the system 100 is in an initial power-up state. Step 1302 further comprises steps wherein microprocessor 600 detects whether two functional modules 104 have been simultaneously added, one to each side of the linear array of units. This may be achieved, for example, by detecting simultaneous low values of UNIT_DETECT_L and UNIT_DETECT_R, which are driven low by the added units as described later. If the system is at initial power-up or two functional units have been simultaneously added, step 1400, as described in FIG. 8, is performed, followed by a repeating of step 1302 according to FIG. 7. Otherwise, step 1304 is performed.

Figure 9A:
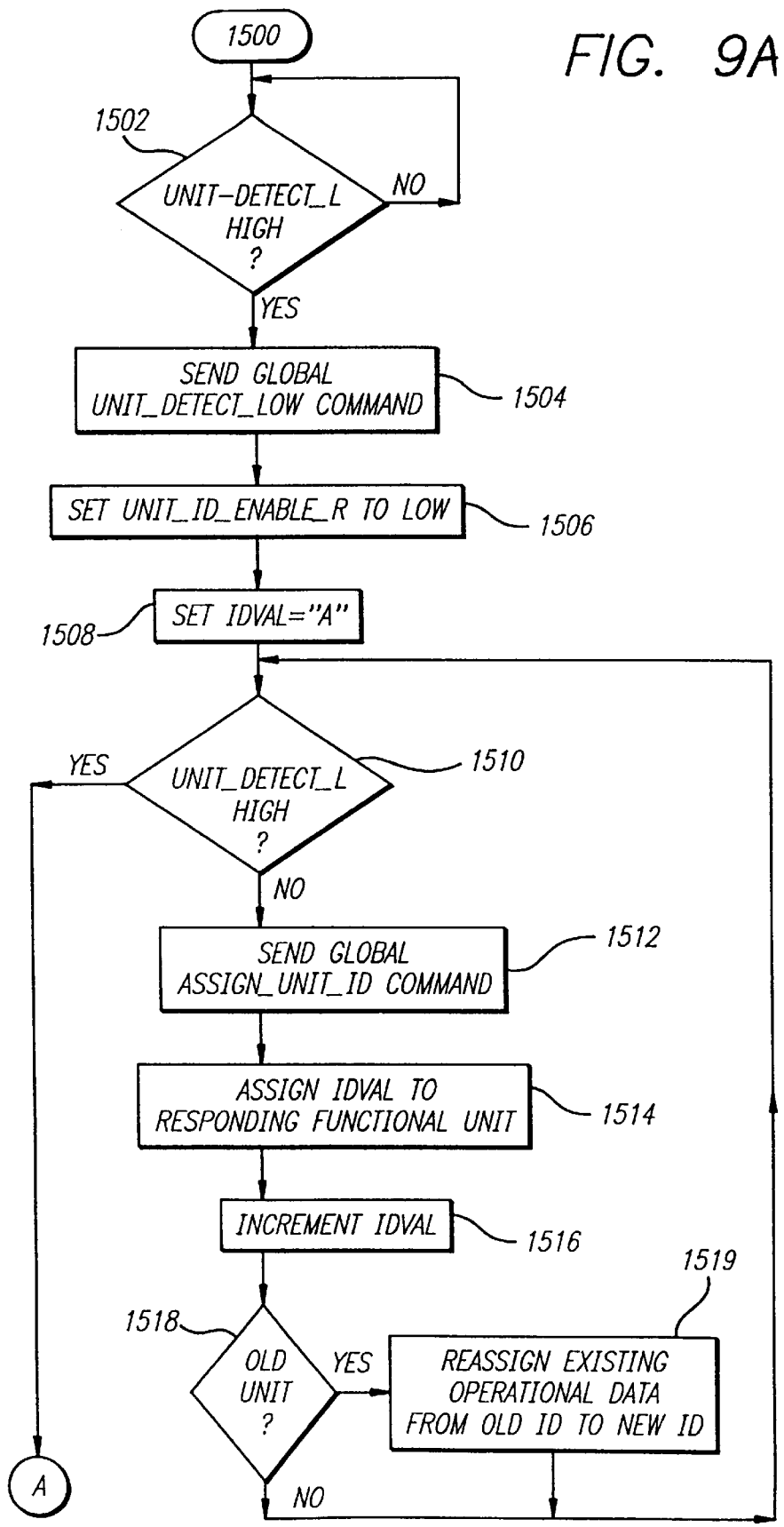
Figure 9B:
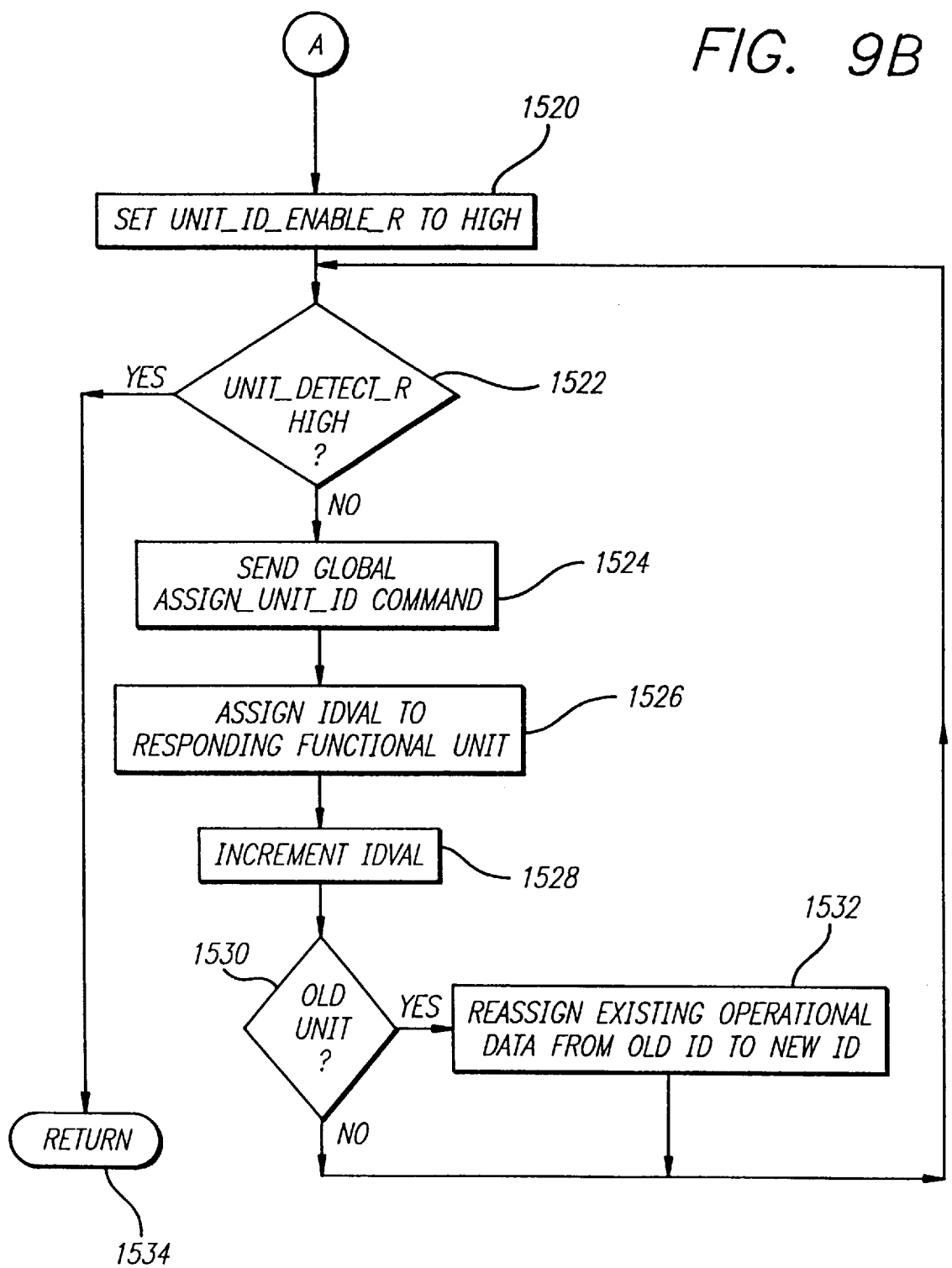

Step 1304 comprises the step of detecting whether a new functional unit has been added to the left side of the linear array of system 100. This is performed by detecting a low value for UNIT_DETECT_L, which is driven low by the added unit as described later. If a unit has been added to the left, step 1500, as shown in FIGS. 9A and 9B is performed, followed by a repeating of step 1302 according to FIG. 7. Otherwise, step 1306 is performed.

Figure 10:
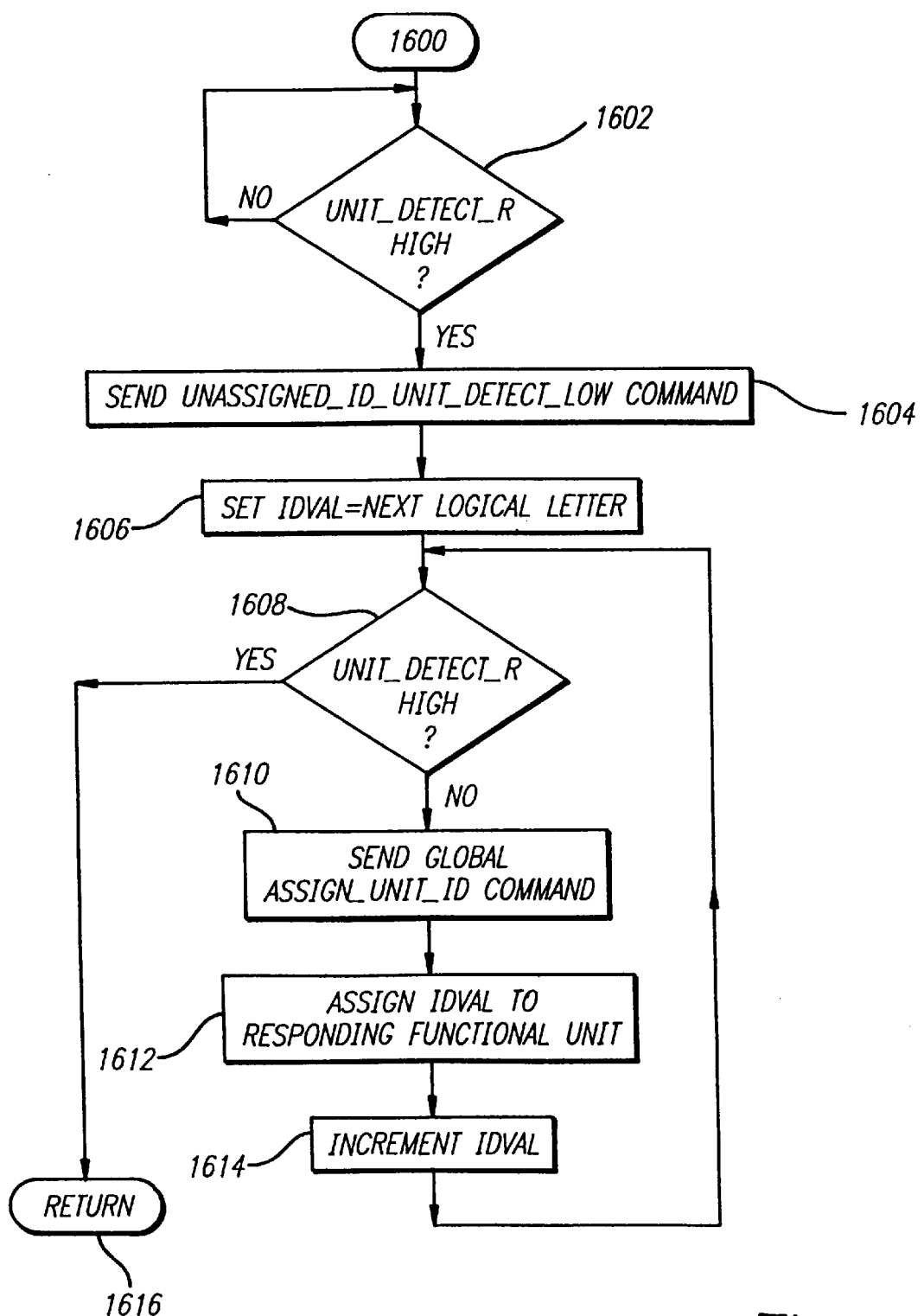

Step 1306 comprises the step of detecting whether a new functional unit has been added to the right side of the linear array of system 100. This is performed by detecting a low value for UNIT_DETECT_R, which is driven low by the added unit as described later. If a unit has been added to the right, step 1600, as described in FIG. 10, is performed, followed by a repeating of step 1302 according to FIG. 7. Otherwise, step 1308 is performed.

Step 1308 comprises the step of detecting whether a functional unit has been detached from the left or right sides. The detachment of a unit may be detected by one or more of three methods. First, a communications time-out with a detached module over the inter-unit communications circuitry may be detected. Second, a change of state of MODDETL or MODDETL may be detected. Third, a high-level communications signal sent by the unit adjacent to the detached unit may be detected, in response to its own detection of a change of state of MODDETL or MODDETR. If a detachment of a functional unit has taken place, step 1310 is performed. Otherwise, step 1302 is performed again in accordance with FIG. 7.

Step 1310 generally comprises the step of determining whether the system is currently in an operational state. If so, the system is placed in an alarm state by step 1312, wherein audio and/or visual alarms may be activated. Otherwise, if the system is not in an operational state, step 1314 is performed, wherein verification by a user is requested by means of visual and audible indications to the user. If verification is not received, the step 1312 alarm steps are followed.

If verification is received, step 1314 is performed, wherein it is determined if the unit has been detached from the left. This information may already have been determined at step 1308. If a unit was detached from the left, step 1500, as shown in FIGS. 9A and 9B is performed, followed by step 1302 according to FIG. 13. Otherwise, a unit has been detached from the right, wherein step 1318, comprising the step of dropping the ID's of the detached unit or units, is performed, followed by step 1302 according to FIG. 7

FIG. 8 illustrates steps carried out by step 1400, which first comprises the step of executing a Power-On-Self-Test (POST) at step 1402. This is followed by step 1404, wherein microprocessor 600 detects whether signals UNIT_

DETECT_L and UNIT_DETECT_R are both high. This will be the case, as described below, when all functional units 104 have completed an analogous POST of their own. Step 1404 repeats until this until both UNIT_DETECT_L and UNIT_DETECT_R are high, wherein step 1406 is performed. At step 1406, a global command is issued by microprocessor 600 instructing all functional unit microprocessors to pull down the unit detect buses 1200L or 1200R by setting their signals PULLDOWN to low. Following step 1406, steps 1408 and 1410 are executed, wherein UNIT_ID_ENABLE_R is set to low, and an internal variable such as IDVAL is set to "A".

Following step 1410, step 1412 is performed, wherein it is determined whether UNIT_DETECT_L is high. If yes, step 1420 is performed. If not, steps 1414, 1416, and 1418 are performed, wherein a global ASSIGN_UNIT_ID command is sent over communications bus 1004, the logical-address IDVAL is assigned to the responding unit, and the value of IDVAL is incremented. It is to be noted that at step 1416, the responding unit is that functional unit which sends a ready-for-ID message across the communications bus 1008. Step 1412 is again performed after step 1418. Thus, sequential logical addresses are assigned to the left units, beginning at the leftmost unit, until all left units have released the left unit detect bus 1200L after receiving their logical ID, thus letting UNIT_DETECT_L be pulled up by pullup source 910.

Step 1420 is entered after UNIT_DETECT_L is pulled up, and comprises the step setting UNIT_ID_ENABLE_R to high to allow units to the right to start receiving logical addresses. Following step 1422, step 1424 is performed, comprising the step of determining whether UNIT_DETECT_R is high. If yes, all functional units to the right, if there are any, have been assigned logical addresses and have released right unit detect bus 1200R, and thus step 1430, which comprises the step of returning to step 1302 according to FIG. 7, is performed. If not, steps 1424, 1426, and 1428 are performed, which are substantially identical to steps 1414, 1416, and 1418 described above. Following these steps, step 1422 is repeated to see if any functional units are still pulling unit detect bus 1200R low. If so, steps 1424, 1426, and 1428 are repeated. If not, step 1430, which comprises the step of returning to step 1302 according to FIG. 7, is performed.

FIGS. 9A and 9B illustrate steps carried out at step 1500 and comprises the step 1502 of determining whether UNIT_DETECT_L is high. As described previously, UNIT_DETECT_L will be high after the unit attached to the left has performed its POST and released unit detect bus 1200L. After UNIT$_{13}$ DETECT_L goes high, steps 1504, 1506, and 1508 are performed, wherein a global command is sent instructing all functional units to pull down unit detect buses 1200L or 1200R, wherein UNIT_ID_ENABLE_R is set to low, and wherein an internal variable such as IDVAL is set to "A".

Following these steps, step 1510 is performed, wherein it is determined whether UNIT_DETECT_L is high. If not, assignment steps 1512, 1514, and 1516, substantially identical to steps 1414, 1416, and 1418 above, are performed. Subsequent to step 1516, step 1518 is performed, which comprises the step of determining whether the unit which has been assigned was an existing unit or is a newly attached unit. This step is performed by simply communicating with the assigned unit and receiving an indicator flag. If the unit is an "old", i.e. existing, unit, step 1520 is carried out in which existing operational data within system 100 corresponding to the old logical address of the unit are reassigned to the new logical address. Otherwise, step 1510 is repeated.

When UNIT_DETECT_L is finally released after assignment of logical units to the left, steps 1520 and 1522, substantially similar in purpose and effect to steps 1420 and 1422 described above, are performed. While the value of UNIT_DETECT_R is low, steps 1524, 1526, 1528, 1530, and 1532 are performed in a manner substantially reflexive to the performance of steps 1510, 1512, 1514, 1516, 1518, and 1520 described above, and according to FIGS. 9A and 9B When UNIT_DETECT_R finally goes high, step 1534, which comprises the step of returning to step 1302 according to FIG. 7, is performed.

FIG. 10 illustrates steps carried out in step 1600 and comprises the step 1602 of determining whether UNIT_DETECT_R is high. If so, all units attached to the right have completed their POST as described above. After UNIT_DETECT_R is detected to be high, steps 1604 and 1606 are performed, wherein a command instructing any unassigned units to pull down unit detect bus 1200R is sent, and a variable IDVAL is assigned to the value of the next logical unit beyond those already assigned. Since step 1600 is entered only if a new unit is attached to the right, only the new units need to be assigned, starting the next logical unit address, and existing units do not need to be reassigned.

Following step 1606, steps 1608, 1610, 1612, and 1614 are performed, which are substantially identical in purpose and effect to steps 1422, 1424, 1426, and 1428 described above and which are performed according to FIG. 10. After UNIT_DETECT_R is released by all the right functional units, the logical address assignment process is complete, and step 1616, comprising the step of returning to step 1302 of FIG. 7, is performed.

Figure 11:
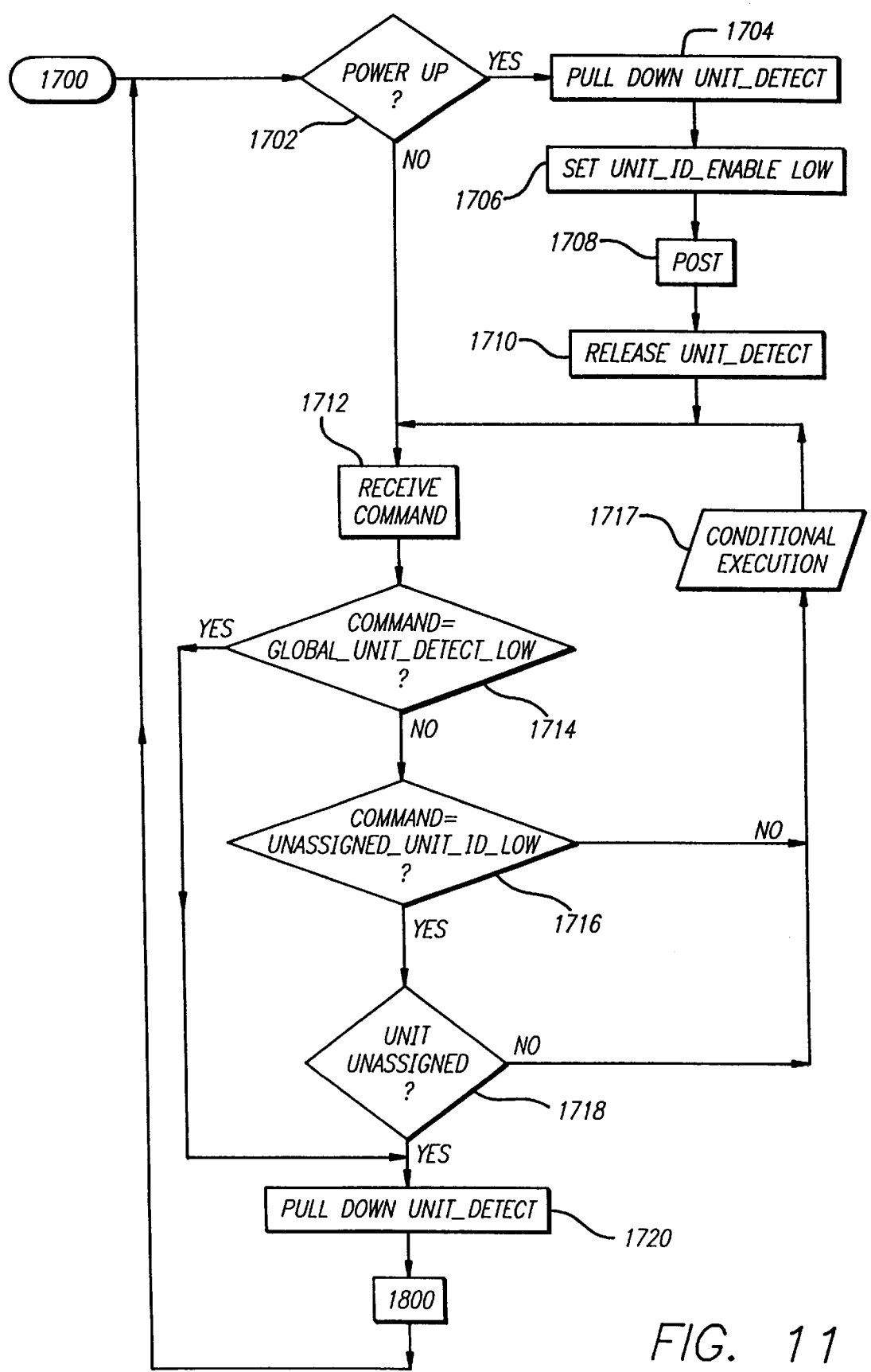
FIGS. 11 and 12 illustrate steps performed by a functional unit of a modular patient care system in accordance with the present invention.

FIG. 11 illustrates steps taken by exemplary functional unit 104A according to the present invention. Beginning at step 1700, step 1702 is entered, wherein it is determined if power has been newly applied to the functional unit, i.e. whether the system 100 is at power-up or whether the functional unit 104A has been newly attached. If not, step 1712 is performed. If so, steps 1704, 1706, 1708, and 1710 are performed, wherein the functional unit pulls down unit detect bus 1200L or 1200R, sets UNIT_ID_ENABLE to low, performs a POST, and then releases unit detect bus 1200L or 1200R. In this manner, interface unit 102 will detect, according to the method described above with reference to FIGS. 7 through 10, either the system initial power-up state or the addition of new functional units. Step 1712 is then performed.

Step 1712 comprises the general step of receiving a command from interface unit 102 according to the general operation of the present invention. Steps 1714 and 1716, which follow step 1712, comprise the steps of combing the incoming commands for certain commands which indicate that a new logical unit address is to be assigned. At step 1714, it is determined whether a global command instructing the unit to pull down unit detect bus 1200L or 1200R has been received. If so, an assignment procedure beginning at step 1720 is performed. If not, step 1716 is performed, wherein it is determined whether a command instructing unassigned units to pull down the unit detect bus 1200L or 1200R has been received. If so, step 1718 is performed. If not, then the incoming command is, at step 1717, either performed or not performed, depending on a variety of factors corresponding to aspects of the system 100 which are beyond the scope of the present disclosure. Following step 1717, the step 1712 of receiving another command is performed.

At step 1718, microprocessor 700 of exemplary functional unit 104A determines whether or not it already has been assigned a logical address. As an example, the exemplary function unit 104A may already have an assigned address where it exists on the right side of interface unit 102 in the linear array of modules, and where an additional functional unit has been added to the right of the linear array. In this case, the interface unit 102 will be assigning logical addresses to the added functional unit but not to the exemplary functional unit 104A. Therefore, the exemplary functional unit 104A will simply proceed with step 1717 as shown in FIG. 11.

If the exemplary functional unit 104A has not been assigned a logical address, assignment steps beginning at step 1720 are performed. At step 1720, the unit detect bus 1200L or 1200R is pulled down by microprocessor 700 by means of signal PULLDOWN as described above. Following this step, step 1800 is performed, followed by a repeating of the step 1702 according to FIG. 11.

Figure 12:
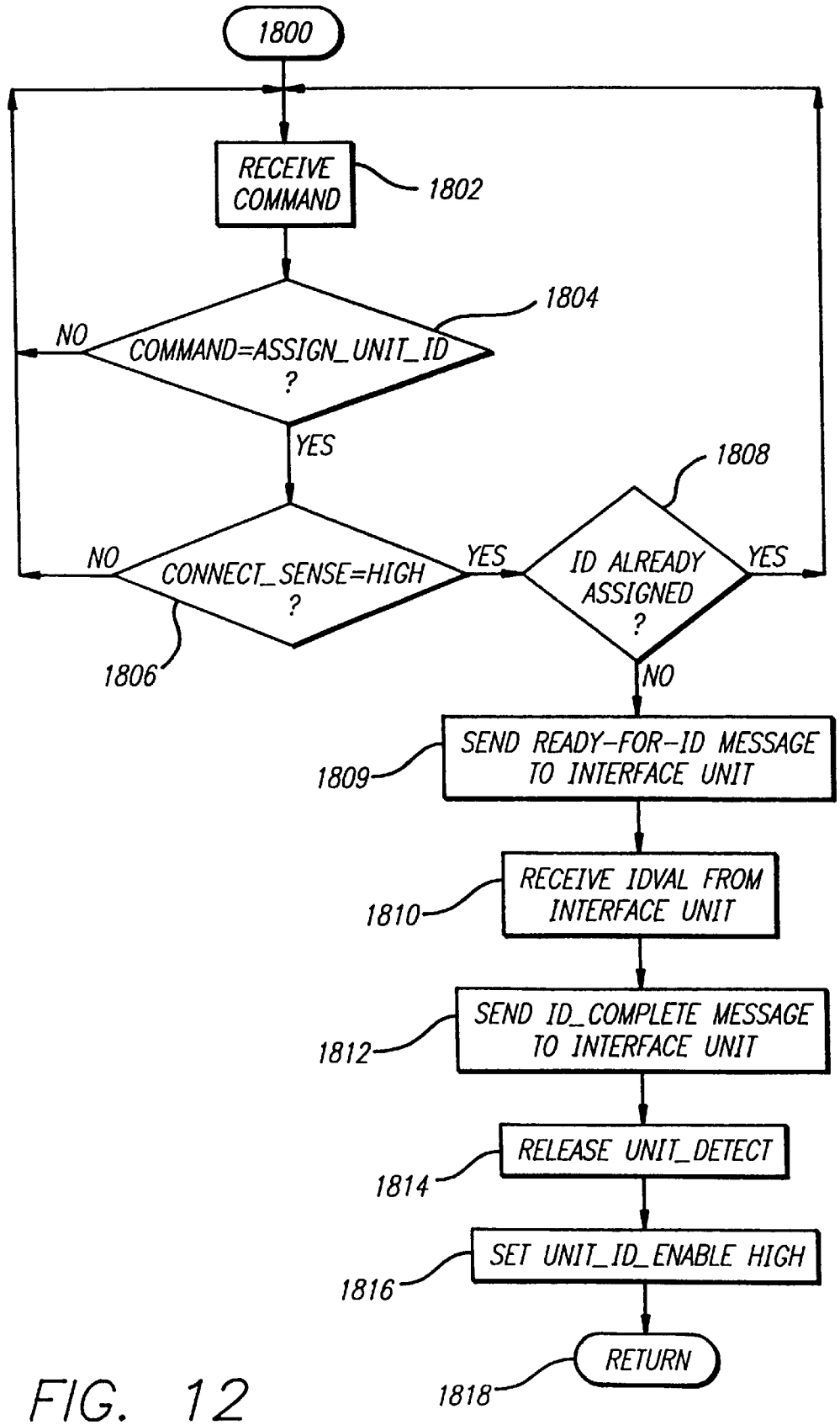

FIG. 12 illustrates steps comprising step 1800 according to the present invention. At step 1802, functional unit 104A receives a command from interface unit 102. Steps 1804, 1806. and 1808 are then performed. As shown in FIG. 12, steps 1804, 1806, and 1808 collectively comprise the steps of determining whether (1) the received command is an ASSIGN_UNIT_ID command, with (2) CONNECT_SENSE being high, (3) at a time when the functional unit has not yet been assigned a logical address after pulling down unit detect bus 1200L or 1200R at step 1720. As described previously with reference to FIGS. 6A and 6B the CONNECT_SENSE signal will only be high if the functional unit is either the leftmost unit, or if the unit immediately to the left of the functional unit has already been assigned a logical ID. Therefore, the presence of all of conditions (1)–(3) above signifies that the functional unit 104A is the leftmost unit which has not yet received a logical address, and furthermore has just received an ASSIGN_UNIT_ID command from the interface unit 102. Responsive to this condition, step 1809 is performed.

Step 1809 comprises the step of sending a ready-for-ID message to the interface unit 102 over the communications bus 1008. Step 1809 is followed by step 1810, which comprises the step of receiving the appropriate logical address IDVAL from interface unit 1810. Following this step, step 1812 is performed, which comprises the step of sending an ID_COMPLETE message to interface unit 102, to indicate that interface unit 102 may proceed with the next unit. Following this, the steps 1814 and 1816 are performed, wherein the unit detect bus 1200L or 1200R is released by the functional unit in question, and wherein UNIT_ID_ENABLE is set to high. Step 1816 is followed by step 1818, which comprises the step of returning to the step 1702 according to FIG. 11.

If the unit in question is not the terminating (i.e. rightmost) functional unit, the setting of UNIT_ID_ENABLE to high causes AND gate 104 to set the ID enable out lead 1018 to high which, in turn, will cause an adjacent functional unit to the right to detect a high state of CONNECT_SENSE. This will thus enable the next functional unit in line to receive the next logical address from the interface unit 102.

It is noted that by releasing the unit detect line 1200L or 1200R, the functional unit 104A would cause the UNIT_DETECT_L or UNIT_DETECT_R signals of interface unit 102 to be pulled up only if all functional units on a given side have released the unit detect line 1200L or 1200R. As described earlier, this is the desired result in order to allow interface unit 102 to assign logical addresses in accordance with the present invention.

Various embodiments of the invention have been described. The descriptions are intended to be illustrative, not limitative. Thus, it will be apparent to those skilled in the art that modifications may be made to the invention as described without departing from the scope of the claims set out below.

What is claimed is:

1. A modular patient care system having a plurality of units detachably coupled to form a linear array of units, said linear array having a originating end and a terminating end, each of said units having an originating side facing said originating end and a terminating side facing said terminating end, said plurality of units comprising:

an interface unit for providing a user interface to said system, said interface unit being capable of providing sequential logical ID's;

a plurality of functional units, each functional unit having a unique resettable logical ID; and a communications bus formed by said linear array of units for allowing each functional unit to communicate with said interface unit and receive commands therefrom;

wherein said patient care system is capable of automatically assigning said sequential logical ID's to said functional units according to their sequential positions in said linear array without requiring external user input or a prearranged locational scheme for indicating a relative physical position of a functional unit.

2. A modular patient care system having a plurality of units detachably coupled to form a linear array of units, said linear array having a originating end and a terminating end, each of said units having an originating side facing said originating end and a terminating side facing said terminating end, said plurality of units comprising:

an interface unit for providing a user interface to said system, said interface unit being capable of providing sequential logical ID's;

a plurality of functional units, each functional unit having a unique resettable logical ID; and a communications bus formed by said linear array of units for allowing each functional unit to communicate with said interface unit and receive commands therefrom;

wherein each functional unit further comprises:

means for detecting a first signal provided by an adjacent originating side unit, said first signal having a first value or a second value different from said first value;

means for providing said first signal to an adjacent terminating side unit;

means for generating a second signal, said second signal being equal to
(a) said first value if the functional unit is at said originating end of the linear array, or
(b) the value of said first signal provided by said adjacent originating side unit if the functional unit is not at the originating end of the linear array;

means for setting said first signal to said second value upon receiving a first command from said interface unit;

means for receiving one of said sequential logical ID's from said interface unit upon detecting said second signal to be equal to said first value after having received said first command;

means for setting said first signal equal to said first value after having received said logical ID;

whereby said patient care system is capable of assigning said sequential logical ID's to said functional units according to their sequential positions in said linear array.

3. The modular patient care system according to claim 2, said system further comprising a unit detect bus formed by said plurality of functional units and said interface unit, said unit detect bus having a first state and a second state different from said first state, each of said functional units further comprising pulling means coupled to said unit detect bus for pulling said unit detect bus to said second state, wherein said interface unit further comprises pulling means capable of pulling said unit detect bus to said first state when none of said functional unit pulling means are pulling said unit detect bus to said second state, wherein each of said functional units further comprises means for pulling said unit detect bus to said second state, and thereafter releasing said unit detect bus, upon initial connection of said functional unit to said linear array of units, and wherein said interface unit further comprises means for detecting said pulling and releasing of said unit detect bus and means for sending said first command to said functional units responsive thereto, whereby said patient care system is capable of assigning sequential logical ID's to said functional units according to their sequential positions in said linear array upon the addition of an added functional module to said linear array.

4. The modular patient care system of claim 2, said system further comprising:

an originating unit detect bus formed by said originating side functional units and said interface unit; and a terminating unit detect bus separate from said originating unit detect bus formed by said interface unit and the set of functional units located on the terminating side of said interface unit, each of said originating and terminating unit detect buses having a first state and a second state different from said first state, each of said functional units further comprising pulling means coupled to said originating or terminating unit detect bus for pulling said originating or terminating unit detect bus to said second state, respectively;

wherein said interface unit further comprises originating side pulling means capable of pulling said originating unit detect bus to said first state when none of said forcing means are pulling said originating unit detect bus to said second state, wherein said interface unit further comprises terminating side pulling means capable of pulling said terminating unit detect bus to said first state when none of said forcing means are pulling said terminating unit detect bus to said second state, wherein each of said functional units further comprises means for pulling said originating or terminating unit detect bus to said second state, and thereafter releasing said originating or terminating side unit detect bus, upon initial connection of said functional unit to said originating or terminating end, respectively, of said linear array of units, and wherein said interface unit further comprises means for detecting said pulling and releasing of said originating or terminating unit detect bus, and means for sending said first command to said functional units responsive to a pulling and releasing of said originating bus and means for sending a second command responsive to said pulling and releasing of said terminating unit detect bus, whereby said patient care system is capable of initiating a logical address assignment procedure upon the addition of a new functional unit to said linear array of units.

5. The modular patient care system of claim 4, wherein said functional units further comprise means for pulling said originating or terminating unit detect bus to said second state upon receiving said first command from said interface unit, wherein said functional units further comprise means for releasing said originating or terminating unit detect bus upon receiving said logical ID and setting said second signal equal to said first value, wherein said interface unit comprises means for detecting the releasing of said originating unit detect bus to said first state after all originating side functional units have released said originating unit detect bus, and means for providing said first signal to an adjacent terminating side unit, said first signal being equal to said first value upon said detection of the releasing of said originating unit detect bus;

whereby said patient care system is capable of assigning sequential logical ID's to said all of said functional units according to their sequential positions in said linear array upon the addition of an added functional module to said originating side of said linear array.

6. The modular patient care system of claim 5, wherein said functional units further comprise means for pulling said originating or terminating unit detect bus to said second state upon both (a) receiving said second command from said interface unit while (b) not yet having an ID assigned, wherein said interface unit further comprises a means for storing the number of functional units already having logical ID's, whereby said modular patient care system is capable of assigning sequential logical ID's to functional modules added to the terminating end of the linear array without reassigning logical ID's to those functional modules already in the linear array.

7. The modular patient care system of claim 6, said interface unit further comprising:

a memory for storing functional unit specific information for at least one of said functional modules indexed according to the logical ID of said at least one functional unit;

means for transferring the functional unit specific information corresponding to said at least one functional unit in said memory to a next sequential logical ID subsequent to the addition of said added unit to said originating side.

8. The modular patient care system of claim 6, said first signal being an ID enable out signal, said first value being a logic high voltage signal, said second value being a logic low voltage signal, said means for detecting said first signal being an ID enable in lead, said means for generating said second signal comprising a pullup resistor coupled between said ID enable in lead and a constant voltage source, wherein said ID enable in lead is pulled up to said logic high voltage signal when not connected to an ID enable out lead of an adjacent originating side unit.

9. The modular patient care system of claim 8, said first command being a global set ID command, said second command being an unassigned unit set ID command, said first state being a logic high voltage, said second state being a logic low voltage, said pulling means of each of said functional units comprising a grounding transistor coupled between a ground and said originating or terminating unit detect buses, said releasing means of each of said functional units comprising said grounding transistor, said interface unit originating side pulling means comprising:

an originating unit detect lead for coupling to said originating unit detect bus; and a left pullup resistor coupled between said originating unit detect lead and a constant voltage source;

wherein said originating unit detect lead is pulled high by said left pullup resistor upon release of said unit detect bus by all of said releasing means.

10. A modular patient care system having a plurality of units detachably coupled to each other to form a linear array, said linear array having a originating end and a terminating end, said units each having an originating side facing said originating end and a terminating side facing said terminating end, said linear array comprising:

an interface unit for providing a user interface to said system;

a plurality of functional units, each functional unit being capable of providing patient therapies or monitoring, each functional unit having a unique resettable logical ID, each functional unit comprising:

a communications bus portion for forming a common communications bus;

a unit detect bus portion for forming a unit detect bus;

means for providing an id_enable_out signal to a unit abutting said terminating side, said id_enable_out signal having a value ENABLE or DISABLE;

means for generating an id_enable_in signal, wherein said id_enable_in signal is equal to (a) ENABLE if the functional unit is at said originating end of said linear array, or (b) the id_enable_out signal of a unit abutting said originating side otherwise;

means for receiving commands from said interface unit over said communications bus;

means for pulling down said unit detect bus to a LOW state and setting said_id enable_out signal to DISABLE responsive to a first command from said interface unit;

means for detecting the state of said id_enable_in signal;

means for receiving a unique logical address from said interface unit upon (1) having received said first command, and (2) detecting the state of id_enable_in to equal ENABLE;

means for setting said logical ID equal to said unique logical address; and means for setting said id_enable_out signal to ENABLE and for releasing said unit detect bus upon setting said logical ID;

whereby said patient care system is capable of assigning sequential logical ID's to said functional modules according to their respective positions in said linear array.

11. The modular patient care system of claim 10, wherein said interface unit comprises:

means for pulling said unit detect bus to a high logic state;

a communications bus portion for forming said common communications bus among said units;

means for detecting said LOW state of said unit detect bus upon initial power-up or upon the addition of a new functional unit;

means for detecting the releasing of said unit detect bus;

means for transmitting a PULL_UNIT_ID_LOW command over said communications bus responsive to said LOW state and said releasing of said unit detect bus;

means for assigning sequential logical addresses to said functional units during a period in which said unit detect bus is pulled LOW.

12. In a modular patient care system having a plurality of units detachably coupled to form a linear array of units having an originating end and a terminating end, each unit having an originating side facing said originating end and a terminating side opposite said originating end, the linear array of units comprising an interface unit for providing sequential logical ID's and a plurality of functional units requiring an assignment of a one of said sequential logical ID's, a method comprising the steps of:

generating a value ENABLE or DISABLE at an ID enable in lead of each functional unit;

transmitting a sequential logical ID to all functional units over a common communications bus formed by functional units and the interface unit;

receiving the sequential logical ID at that functional unit which (1) detects a value ENABLE at its ID enable in lead, and (2) has not yet been assigned a logical ID;

setting an ID enable out lead of that functional unit to the value ENABLE after receiving the sequential logical ID, for generating the value ENABLE at the ID enable in lead of an adjacent terminating side unit.

13. The method of claim 12, each functional unit having a pullup resistor connected between the ID enable lead and a constant voltage source with the value ENABLE, the step of generating the value ENABLE or DISABLE at the ID enable in lead comprising the step of (1) if the functional unit is at the originating end of the linear array, pulling up the value at the ID enable in lead to ENABLE, and (2) otherwise, connecting the ID enable in lead to the ID enable out lead of the originating side adjacent unit to assume the value of the ID enable out lead of the originating side adjacent unit.

14. The method of claim 13, further comprising the steps of:

determining whether an additional unit has been added to the originating end of the linear array;

determining whether an additional unit has been added to the terminating end of the linear array;

if an additional unit has been added to the originating end of said linear array, assigning sequential logical ID's to all functional units;

if the additional unit has been added to the terminating side of said linear array, assigning a sequential logical ID only to the additional unit.

15. The method of claim 14, said step of determining whether an additional unit has been added to the originating end of the linear array comprising the step of detecting a pulling down, followed by a releasing, of an originating unit detect bus formed by the originating functional units and the interface unit, the originating functional units being those units on the originating side of the interface unit, the originating unit detect bus being capable of being pulled up by the interface unit upon being released by all originating functional units, the added functional unit being capable of pulling down and then releasing the originating unit detect bus on power-up.

16. The method of claim 15, said step of determining whether an additional unit has been added to the terminating end of the linear array comprising the step of detecting a pulling down, followed by a releasing, of an terminating unit detect bus formed by the terminating functional units and the interface unit, the terminating unit detect bus being capable of being pulled up by the interface unit upon being released by all terminating functional units, the added functional unit being capable of pulling down and then releasing the terminating unit detect bus on power-up.

17. The method of claim 16, said step of assigning sequential logical ID's to all functional units comprising the steps of:

sending a first command to all functional units instructing each unit to pull down the originating or terminating unit detect bus to which it is connected;

setting an interface unit ID enable out lead to the value DISABLE, the interface unit ID enable out lead being coupled to the ID enable in lead of an adjacent terminating side functional unit;

assigning sequential logical ID's to all originating side functional units;

detecting when all originating side functional units have been assigned logical ID's;

setting the interface unit ID enable out lead to ENABLE;

assigning sequential ID's to all terminating side functional units.

18. The method of claim 17, each functional unit being capable of releasing the unit detect bus to which it is connected upon receiving a sequential logical ID, the step of detecting when all originating side functional units have been assigned logical ID's comprising the step of detecting the releasing of the originating unit detect bus.

19. A computer-readable medium which can be used to direct an interface unit of a modular patient care system to assign sequential logical unit ID's to a plurality of functional units attached to the interface unit so as to form a linear array of units having an originating end and a terminating end, the interface unit and the functional units each having an originating side facing the originating end and a terminating side opposite the originating side, the computer-readable medium comprising:

means for directing the interface unit to send commands and receive information over a common communications bus formed by the interface unit and the attached functional units;

means for directing the interface unit to detect system power-up or the attachment of additional functional units and for directing the interface unit to send a first command to all attached functional units responsive thereto;

means for directing the interface unit to transmit sequential logical ID's to all functional units over the common communications bus, for receiving by a single functional module which has (1) received the first command, (2) received an enabling signal from an originating side adjacent unit or is the functional unit at the originating end, and (3) has not yet received a logical ID after receiving the first command;

means for directing the interface unit to detect when all originating side functional units have received logical ID's and for directing the interface unit to transmit an enabling signal to a terminating side adjacent functional unit responsive thereto.

20. The computer-readable medium of claim 19, the means for directing the interface unit to detect the attachment of additional functional units further comprising:

means for directing the interface unit to detect a pulling and releasing of a voltage signal present at an originating unit detect bus lead, the originating unit detect bus lead for contacting an originating unit detect bus formed by the originating side functional units, each functional unit being capable of pulling the originating unit detect bus to a second voltage, each functional unit also being capable of releasing the originating unit detect bus, the originating unit detect bus lead being connected to a constant first voltage through a pullup resistor in the interface unit, whereby the first voltage is present at the originating unit detect bus lead only when no originating side functional module is pulling the originating unit detect bus to the second voltage, wherein each functional unit is capable of pulling and then releasing said originating unit detect bus upon initial attachment to the originating end of the linear array; and means for directing the interface unit to detect a pulling and releasing of a voltage signal present at a terminating unit detect bus lead, the terminating unit detect bus lead for contacting a terminating unit detect bus formed by the terminating side functional units, each functional unit being capable of pulling the terminating unit detect bus to a second voltage, each functional unit also being capable of releasing the terminating unit detect bus, the terminating unit detect bus lead being connected to a constant first voltage through a pullup resistor in the interface unit, whereby the first voltage is present at the terminating unit detect bus lead only when no terminating side functional module is pulling the terminating unit detect bus to the second voltage, wherein each functional unit is capable of pulling and then releasing said terminating unit detect bus upon initial attachment to the linear array.

21. The computer-readable medium according to claim 20, the means for directing the interface unit to detect when all originating side functional units have received logical ID's comprising:

means for directing the interface unit to transmit as the first command a command directing all functional units to pull the originating or terminating unit detect bus to the second value; and means for directing the interface unit to detect the state of the originating unit detect lead subsequent to transmitting the first command, said functional modules being capable of releasing the originating or terminating unit detect bus upon being assigned a logical ID, whereby the originating unit detect lead will contain the first voltage after all originating side units have been assigned logical ID's.

22. A computer-readable medium which can be used to direct a functional unit of a modular patient care system in receiving a sequential logical unit ID from an interface unit, the modular patient care system having a plurality of functional units attached to the interface unit so as to form a linear array of units having an originating end and a terminating end, the interface unit and the functional units each having an originating side facing the originating end and a terminating side opposite the originating side, the computer-readable medium comprising:

means for directing the functional unit to pull and then release a unit detect bus upon initial power-up of the functional module, the unit detect bus formed by the functional unit and other functional units, each of the functional units being capable of pulling the unit detect bus to a second voltage, each functional unit also being capable of releasing the originating unit detect bus;

means for directing the functional unit to sense the voltage of an ID enable in lead, the voltage having the value ENABLE or DISABLE, the ID enable in lead being for connecting to and assuming the value of an ID enable out lead of an adjacent originating unit side functional unit, the ID enable in lead being configured so as to have the value ENABLE if the functional module is at the originating end;

means for directing the functional unit to receive a first command from the interface unit over a common communications bus and for pulling the unit detect bus to the second value responsive thereto;

means for directing the functional unit to receive a unique sequential logical ID from the interface unit upon (1) having received the first command, and (2) detecting the voltage of the ID enable in lead to be ENABLE;

means directing the functional unit to set an internal logical address equal to the value of the sequential logical ID;

means for directing the functional unit to release the unit detect bus after receiving the logical ID; and means for directing the functional unit to set the value of the ID enable out lead to ENABLE after receiving the logical ID.

* * * * *